United States Patent [19]

Renschler et al.

[11] Patent Number: 5,814,525
[45] Date of Patent: Sep. 29, 1998

[54] PIEZOELECTRIC BIOSENSOR WITH A LADDER POLYMER SUBSTRATE COATING

[75] Inventors: Clifford L. Renschler, Tijeras; Christine A. White, Albuquerque, both of N. Mex.; Robert M. Carter, New Orleans, La.

[73] Assignee: Sandia Corporation, Albuquerque, N. Mex.

[21] Appl. No.: 591,936

[22] Filed: Jan. 25, 1996

[51] Int. Cl.⁶ .................. G01N 33/551; G01N 33/552
[52] U.S. Cl. .............. 436/524; 310/311; 310/312; 310/313 R; 310/340; 427/2.1; 427/2.13; 427/100; 427/240; 427/372.2; 427/374.1; 427/377; 427/384; 427/414; 422/82.01; 435/287.1; 435/287.2; 435/287.9; 436/518; 436/527; 436/532; 436/806
[58] Field of Search .................. 310/311, 312, 310/313 R, 340; 427/2.1, 2.13, 100, 240, 372.2, 374.1, 377, 384, 414; 422/82.01; 435/287.1, 287.2, 287.9; 436/518, 524, 527, 532, 806

[56] References Cited

U.S. PATENT DOCUMENTS

| | | | |
|---|---|---|---|
| 4,236,893 | 12/1980 | Rice | 310/312 |
| 4,242,096 | 12/1980 | Oliveira et al. | 310/312 |
| 4,735,906 | 4/1988 | Bastiaans | 436/527 |
| 4,789,804 | 12/1988 | Karube et al. | 310/311 |
| 4,847,193 | 7/1989 | Richards et al. | 435/6 |
| 4,999,284 | 3/1991 | Ward et al. | 435/4 |
| 5,001,053 | 3/1991 | Takahashi et al. | 435/810 |

*Primary Examiner*—Christopher L. Chin
*Attorney, Agent, or Firm*—Timothy D. Stanley

[57] ABSTRACT

A piezoelectric biosensor substrate useful for immobilizing biomolecules in an oriented manner on the surface of a piezoelectric sensor has a ladder polymer of polyacrylonitrile. To make the substrate, a solution of an organic polymer, preferably polyacrylonitrile, is applied to the surface of a piezoelectric sensor. The organic polymer is modifying by heating the polymer in a controlled fashion in air such that a ladder polymer is produced which, in turn, forms the attachment point for the biomolecules comprising the piezoelectric biosensor.

17 Claims, 2 Drawing Sheets

PIEZOELECTRIC BIOSENSOR WITH A LADDER POLYMER SUBSTRATE COATING

STATEMENT OF GOVERNMENT INTEREST

This invention was made with Government support under contract no. DE-AC04-94AL85000 awarded by the U.S. Department of Energy to Sandia Corporation. The U.S. Government has certain rights in the invention.

BACKGROUND OF THE INVENTION

This invention pertains generally to biochemical sensors and more particularly to the use of thermally modified organic polymers as a substrate for biochemical sensors.

Determining or monitoring the presence of certain chemical species such as pollutants, toxic substances and biohazards, including pesticides and organophosphorous-based products, in extremely low concentrations is becoming of increasing importance in such diverse fields as defense, health, environmental protection, resource conservation and chemical processes.

There presently exist very sophisticated and complicated systems which are capable of detecting the presence of pico ($10^{-12}$) grams of a material. However, these devices are, for the most part, impractical for field applications. Because they are so very precise, these instruments are very sophisticated, require substantial capital investment, generally take a long time to perform an analysis and require a highly trained and dedicated staff to operate the equipment and interpret the data.

Biochemical sensors can provide less expensive but highly sensitive (with sensitivities as low as $10^{-10}$M) means for determining and/or monitoring the presence of various chemical species in an environment. The conditions necessary for a suitable biochemical sensor have been summarized by Dave et al, *Sol-Gel Encapsulation Methods for Biosensors*, Anal. Chem., 66, November 1994, p.1121A. By nature, many biological macromolecules, such as enzymes and antibodies, hereinafter referred to as biomolecules, are highly efficient at recognizing specific materials in aqueous media. The quintessential biosensor consists of an immobilized biomolecule that binds or otherwise reacts with a specific analyte coupled with some type of signal transducer or sensing device such as an electrode, optical fiber or piezoelectric material, which generates a signal proportional to the quantity of analyte bound. Furthermore, optimum biosensor design requires maximum retention of biomolecular activity as well as efficient and cost-effective signal transduction.

An extensive discussion of biochemical sensors is found in Gopel et al, *Sensors a Comprehensive Survey*, III, 1992, pp. 717–819. Two of the more prevalent sensing devices or signal transducers for biosensors are electrochemical and piezoelectric. While electrochemical-based biosensors offer advantage in the areas of sensitivity and quantitation they suffer from the disadvantage that it is necessary to provide means for electron transfer between the biomolecule and the electrode upon which they are supported, generally by providing an electrically conducting substrate for the biomolecule such as a metal or carbon. A further disadvantage of electrochemical-based biosensors is that their use is confined to a liquid, generally aqueous, environment. Other problems associated with the use of electrochemical-based biosensors are interferences, related to electrochemical reaction of species other than the one(s) of interest, and fouling.

Piezoelectric-based biosensors, on the other hand, operate on the basis of their ability to detect minute changes in mass in a coating formed on the device surface, wherein the coating can comprise a substrate which attaches the sensing biomolecule to the surface of the piezoelectric biosensor. Consequently, these devices can be used in either a gaseous or aqueous environment. The class of piezoelectric-based biosensors can be further subdivided into surface acoustic wave (SAW), acoustic plate mode (APM), or quartz crystal microbalance (QCM) devices depending on their mode of detection of mass changes. SAW sensors employ an alternating voltage to an interdigital transducer formed on the piezoelectric crystal to generate a surface acoustic wave. The propagation velocity of this surface wave is a sensitive probe of changes in the properties of a surface coating material such as mass, elasticity, viscoelasticity, conductivity and dielectric constant. Thus, changes in any of these coating properties results in changes in the attenuation of the surface acoustic wave. That is, when a substance sorbs or is otherwise caused to adhere to a coating formed on the surface on the surface of a SAW device, a corresponding response is produced. APM devices operate on a similar principle to SAW devices except that the acoustic wave used can be operated with the device in contact with a liquid. Similarly, an alternating voltage applied to the two opposite electrodes on a QCM (typically AT-cut quartz) device induces a thickness shear wave mode whose resonance frequency changes in proportion to mass changes in a coating material. While these piezoelectric devices are very sensitive detectors, especially for mass, and piezoelectric-based biosensors are becoming a tool to provide a fast, direct and relatively inexpensive method for real-time measurement of biomolecular reaction, they are not inherently selective with respect to different substances. Therefore, in order to make the devices selective for particular substances, biomolecules which have defined specificities can be incorporated into the surface coating.

In general, a biomolecule can be bound (or immobilized) in some fashion to a substrate or coating on the surface of the piezoelectric-based biosensors. As an analyte solution containing, for example, an antigen or antibody is passed over the surface of the piezoelectric-based biosensor, antigen or antibody molecules specific to the biomolecule (antibody or antigen) attached to the surface coating on the piezoelectric biosensor are chemically bound to the biomolecule thereby causing an increase in weight which is detected by the piezoelectric element.

A disadvantage associated with piezoelectric biosensors is that the substrate material on the piezoelectric surface can react with or be attacked by the biological materials in the analyte solution, thereby giving false results and/or degrading the substrate. Further, the inability to orient the biomolecules attached to the substrate such that more biologically active binding sites are available to the analyte reduces the efficiency and raises the minimum detection level of piezoelectric biosensors. Another disadvantage with piezoelectric biosensors is the difficulty of removing analyte from the biomolecule attached to the piezoelectric sensor (a process termed chaotroping) without degrading the biomolecules attached to the substrate. What is needed to solve these problems is a piezoelectric biosensor that has a substrate that is unreactive to nonbiological materials contained in the analyte solution, that provides a means for orienting biomolecules (antigen or antibody) attached to the substrate, thereby increasing the number of binding sites by increasing the number density of biomolecules attached to the substrate, and that further provides for chaotroping the piezoelectric biosensor without degrading the biomolecules attached to the piezoelectric biosensor thereby providing for reuse of the biosensor and reducing cost per test.

Responsive to these needs, the present invention provides a method for attaching biomolecules to the surface of a piezoelectric sensor wherein a solution of an organic polymer is applied to the surface of a piezoelectric sensor, the organic polymer is thermally modified thereby forming a substrate for attaching biomolecules to the surface of piezoelectric-based biosensors.

SUMMARY OF THE INVENTION

The present invention provides a novel method for preparing a piezoelectric biosensor substrate useful for attaching biomolecules to the surface of a piezoelectric material, preferably a quartz crystal microbalance, by applying a solution, preferably by spin casting, of an organic polymer, preferably polyacrylonitrile (PAN), to the surface of the piezoelectric material, thermally modifying the organic polymer and then attaching the desired biomolecule reagent to the modified organic polymer. The step of modifying comprises heating an organic polymer in a controlled way such that a ladder polymer is produced which, in turn, forms the attachment point for those biomolecules or cross-linking ragents comprising the piezoelectric biosensor.

In accordance with this invention, a novel and more efficient piezoelectric biosensor substrate can be prepared by:
  a) applying a solution of an organic polymer, preferably polyacrylonitrile (PAN) dissolved in dimethyl formamide (DMF), to the surface of a piezoelectric crystal by spin coating in an atmosphere wherein the relative humidity is at least 40% and preferably 80%;
  b) evaporating the DMF solvent at room temperature and at 80% humidity to form a PAN film on the surface of the piezoelectric crystal; and
  c) modifying the PAN film by heating the piezoelectric crystal/PAN film combination in a controlled fashion to form a ladder polymer.

DETAILED DESCRIPTION OF THE INVENTION

The present invention provides a method for thermally modifying organic polymers such that they are particularly useful as substrate materials for immobilizing biomolecules on piezoelectric biosensors.

It is known in the art that various organic polymers can be thermally modified to form ladder polymers. By virtue of their unique structure and chemical properties, this invention recognizes that these modified organic materials, hereinafter ladder polymers, provide a means to immobilize or attach sensor biomolecules to a sensor surface wherein the sensor biomolecules are caused to be oriented in a substantially vertical orientation thereby increasing the number density of biomolecules and thus providing for the analyte to have access to a higher number of biologically active binding sites such that the piezoelectric biosensor that has a faster response time and is sensitive to lower concentrations of analyte.

Figure 1:
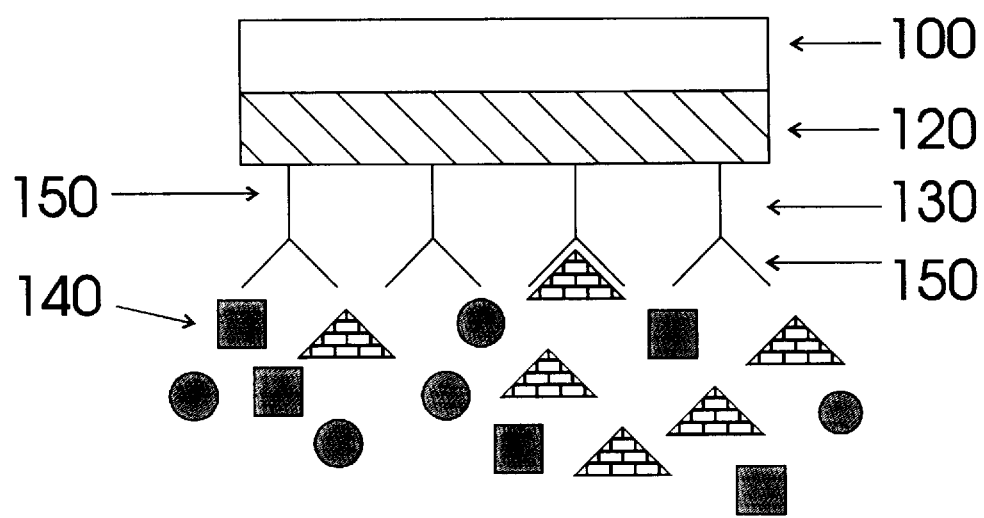
FIG. 1 shows a typical configuration of a piezoelectric biosensor according to the invention.

To better appreciate the scope of the present invention, the following introductory comments are provided. Biosensors can be formed by immobilizing a biomolecule that binds or otherwise reacts with a specific analyte onto a substrate, where the substrate resides on the surface of some type of signal transducer which generates a signal in proportion to the extent of reaction. Referring now to FIG. 1, sensing element 100 is coated with a substrate 120 that serves both to immobilize sensor biomolecules 130 and attach them to sensing element 100. Conventional methods of sensor biomolecule immobilization include covalent bonding, physical absorption or cross-linking to a suitable carrier matrix, or trapping or encapsulating the sensor biomolecule in or onto a semipermeable membrane.

It has been discovered that in order to achieve optimum performance from biosensors, in general, and piezoelectric biosensors, in particular, it is desirable to immobilize the sensor biomolecules in such a manner so as to create a favorable orientation of the sensor biomolecules with respect to an analyte solution, wherein that portion of the sensor biomolecule which binds or otherwise reacts with the analyte is oriented substantially toward the analyte 140, the rest of the sensor biomolecule being attached to the substrate. By causing the sensor biomolecules to be arranged in a substantially vertical orientation, the number of biologically active binding sites (i.e., that part of the biomolecule that binds or otherwise reacts with the analyte) 150 is increased thereby providing for not only a lower detection limit but also a more rapid response. The inventors have discovered a unique class of organic polymers that provide for attaching and orienting sensor biomolecules in a desirable orientation.

It is well known in the art that there exist certain regions or portions in an organic molecule which can act as electron acceptors or electron donors and as such can attract to these specific regions or portions those parts of a second organic molecule which can donate or accept electrons. What has been discovered is that certain organic polymers, known as ladder polymers, possess the ability to immobilize sensor biomolecules in an orientation preferable for application to piezoelectric biosensors. It has been discovered that a robust chemical bond can be formed between the ladder polymer formed from polyacrylonitrile and sensor biomolecules. In the case of polyacrylonitrile (PAN), the ladder polymer provides a —C=N— site for bonding the carboxylic acid group(s) that comprise the tail end of typical sensor biomolecule, such as an antibody. Thus any sensor biomolecule that has an available carboxyl group or which can be substituted to form a carboxyl group can be immobilized in this way. Further, any sensor biomolecule that contains a group(s) that can interact directly with the nitrogen backbone of the ladder polymer or the ladder polymer itself, FIG. 2, can provide for attachment for the sensor biomolecule. In this way antibody molecules are immobilized by binding the Fc portion of the antibody to the ladder polymer PAN substrate, either directly or by means of a cross-linking reagent which can form a covalent bond between PAN and the biomolecule, such that their active binding sites are oriented substantially away from the substrate structure, thereby making them easily accessible to any corresponding antigens that may be present in the analyte solution.

It will be appreciated that ladder polymers are well known in the art and are defined as those polymers which consist of an uninterrupted series of aromatic ring structures connected by links around which no bond rotation can take place except by bond breaking, Billmeyer, ibid., p. 427. These polymers are typically formed by a process of thermal degradation of a parent organic molecule.

Figure 2:
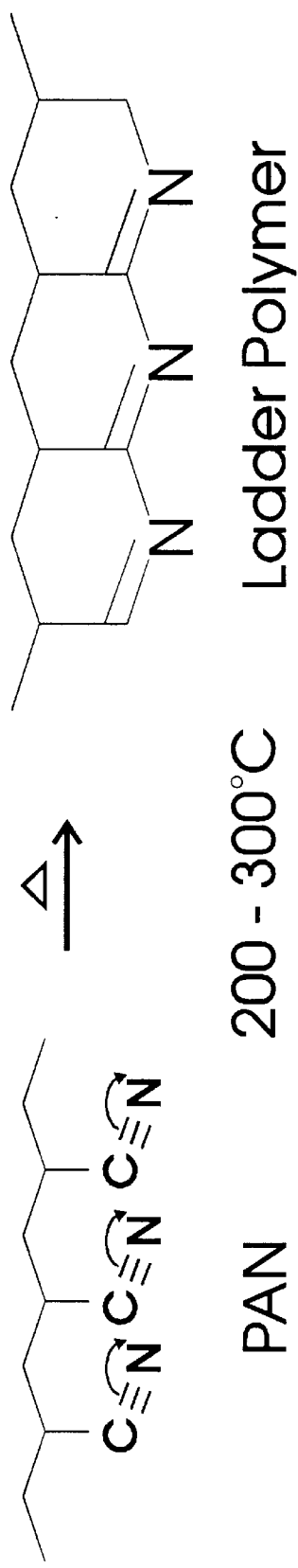
FIG. 2 shows the structure of a typical ladder polymer useful as a substrate for the piezoelectric biosensor of FIG. 1.

Although it is a complex system, the chemistry associated with the thermal degradation of PAN has been extensively investigated. It is generally accepted that PAN undergoes an intramolecular reaction that leads to fused, conjugated cyclic structures down the chain length (referred to as a "ladder polymer") and that this ladder polymer rapidly reacts with oxygen to form the final brown/black "preoxidized" or "stabilized" ladder polymer as shown in FIG. 2. However, the overall pretreatment step is quite exothermic; without careful control of processing conditions the polymeric precursor material can become so hot that it may fuse, decompose or even burn. Consequently, it has been discovered that in order to prepare a PAN ladder polymer suitable for use as a substrate for piezoelectric biosensors, it is necessary that the rate of heating during the PAN pretreatment step be low, between 1°–2° C./min and preferably about 1.6° C./min. Arnold in U.S. Pat. No. 4,832,881, incorporated herein by reference, descrapes conditions appropriate for forming ladder polymers from PAN. In order to accommodate more biosensor molecules, thereby increasing the sensitivity of the piezoelectric biosensor, it is desirable that the surface area of the ladder polymer substrate be large ($\approx 19$ cm$^2$/cm$^2$). This invention recognizes that by controlling the relative humidity during production of the PAN foam, it is possible to control the cell size of the PAN foam. As the relative humidity increases the pore size and the surface area of the foam matrix increases; at a relative humidity of between about 40 and 80% the pore size is $\approx 1$ $\mu$m.

Figure 3:
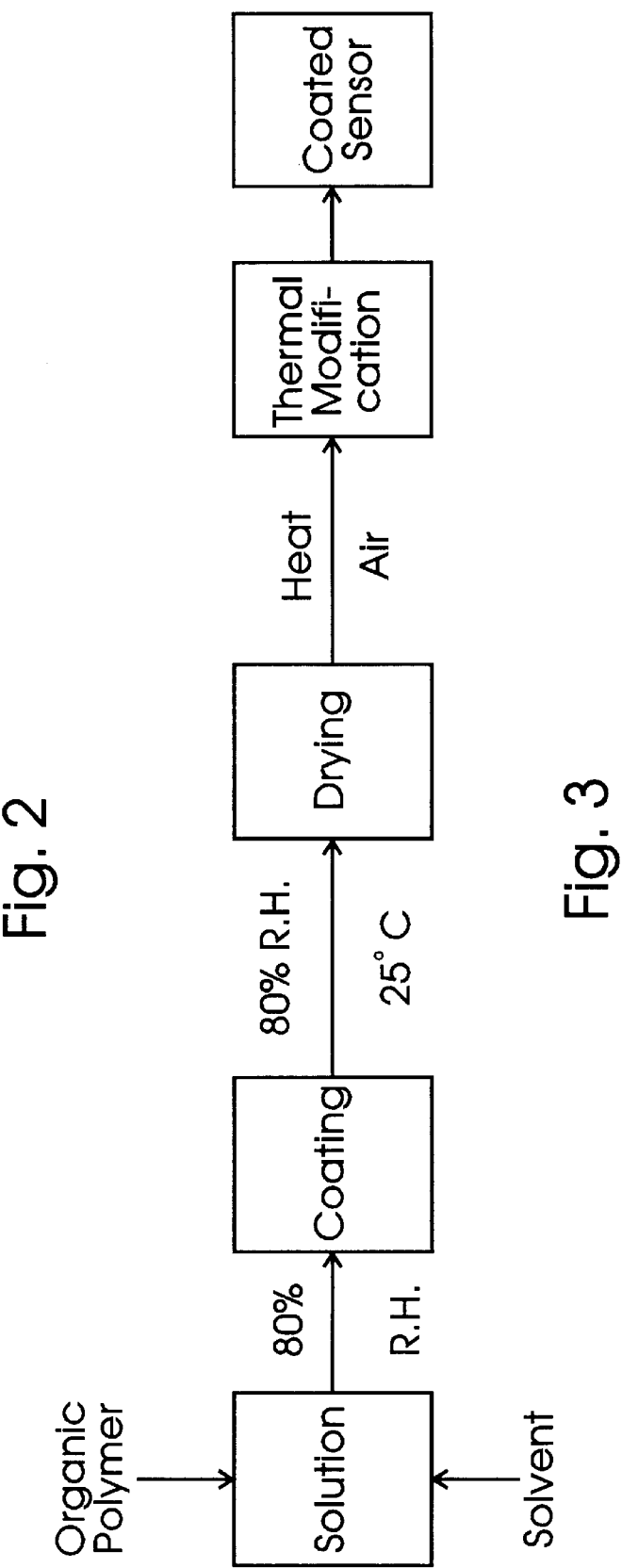
FIG. 3 shows the process for preparing the ladder polymer of FIG. 2.

The present invention can be characterized by the following steps as shown in FIG. 3:

a) dissolving PAN in a suitable organic solvent;

b) applying the PAN solution at a relative humidity of between about 40% and 80% to the cleaned surface of a piezoelectric crystal by spin-casting to form a film, wherein the thickness of the film is from about 200 Å to about 2 $\mu$m thick and preferably about 4000 Å thick;

c) maintaining the PAN film at room temperature and between 40% and 80% relative humidity until the organic solvent evaporates;

d) modifying the PAN film by heating the film in air at a heating rate of between 1°–2° C./min, preferably at about 1.6° C./min, until the temperature reaches about 220° C. and holding the PAN film at that temperature for about 16 hrs; and e) cooling the pretreated film to room temperature at a cooling rate of between 1°–2° C./min, preferably at about 1.6° C./min.

From the foregoing description, one skilled in the art can readily ascertain the essential characteristics of the present invention. The description is intended to be illustrative of the present invention and is not to be construed as a limitation or restriction thereon, the invention being delineated in the following claims.

We claim:

1. A piezoelectric-based biosensor, comprising:
   a piezoelectric sensing element;
   a substrate coating on said piezoelectric sensing element, wherein the substrate coating comprises a ladder polymer; and
   at least one biomolecule immobilized onto said substrate coating for the purpose of sensing at least one analyte species.

2. The biosensor of claim 1, wherein the ladder polymer is polyacrylonitrile.

3. The biosensor of claim 1, wherein the ladder polymer has been thermally modified by heating the polymer to a temperature of about 220° C. and maintaining the polymer at about 220° C. for about 16 hours.

4. The biosensor of claim 1 wherein each biomolecule has a tail end comprising carboxylic acid groups, the biomolecules being oriented on the substrate in the same direction.

5. The biosensor of claim 4 wherein the ladder polymer provides a —C=N— site for bonding said tail end.

6. The biosensor of claim 1, wherein said substrate coating comprises a single layer.

7. A method for providing a substrate coating on a piezoelectric element for a piezoelectric-based biosensor, comprising the steps of:
   forming an organic polymer solution by dissolving in a solvent an organic polymer capable of forming a series of aromatic ring structures connected by links around which no bond rotation can take place except by bond breaking;
   equilibrating the organic polymer solution at a controlled relative humidity;
   disposing the equilibrated organic polymer solution onto the surface of a piezoelectric element to form a polymer coating;
   evaporating the solvent from the polymer coating at a controlled relative humidity; and
   modifying the organic polymer coating by heating the polymer coating at a controlled rate in air to a selected temperature, maintaining the temperature, thereby transforming the organic polymer to a ladder polymer substrate coating, and cooling the coating at a controlled rate.

8. The method of claim 7 wherein the ladder polymer substrate coating has a thickness between about 200 Å and 2 $\mu$m.

9. The method of claim 7 wherein the piezoelectric element is a quartz crystal microbalance.

10. The method of claim 7 wherein the organic polymer is polyacrylonitrile.

11. The method of claim 7 wherein the solvent is dimethyl formamide.

12. The method of claim 7 wherein the relative humidity is between about 40% and 80%.

13. The method of claim 7 wherein the relative humidity is about 80%.

14. The method of claim 7 wherein said step of disposing is spin-casting.

15. The method of claim 7 wherein said step of modifying comprises heating the organic polymer coating in air to a temperature of about 220° C., and maintaining the polymer temperature of about 220° C. for about 16 hours.

16. A biosensor having a sensor substrate coating prepared by the method of claim 7.

17. A method for making a piezoelectric biosensor, comprising:
   dissolving in a solvent an organic polymer capable of forming a series of aromatic ring structures connected by links around which no bond rotation can take place except by bond breaking;
   equilibrating the organic polymer solution at a controlled relative humidity;
   disposing the equilibrated organic polymer solution onto the surface of a piezoelectric element to form a polymer coating;
   evaporating the solvent from the polymer coating at a controlled relative humidity;
   modifying the organic polymer coating by heating the polymer coating at a controlled rate in air to a selected temperature, maintaining the temperature, thereby transforming the organic polymer to a ladder polymer substrate coating, and cooling the coating at a controlled rate; and
   immobilizing one or more biomolecules onto said substrate coating for the purpose of sensing one or more analyte species.

* * * * *